(12) United States Patent
Ishizaki et al.

(10) Patent No.: US 6,756,219 B1
(45) Date of Patent: Jun. 29, 2004

(54) HUMAN SECRETORY TYPE PHOSPHOLIPASE A$_2$

(75) Inventors: Jun Ishizaki, Osaka (JP); Noriko Suzuki, Osaka (JP); Kohji Hanasaki, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/856,486

(22) PCT Filed: Dec. 7, 1999

(86) PCT No.: PCT/JP99/06844

§ 371 (c)(1),
(2), (4) Date: Jun. 11, 2001

(87) PCT Pub. No.: WO00/34486

PCT Pub. Date: Jun. 15, 2000

(30) Foreign Application Priority Data

Dec. 9, 1998 (JP) .......................................... 10/349608

(51) Int. Cl.$^7$ .......................... C12N 9/18; C12N 15/00; C07H 21/04; A61K 38/46
(52) U.S. Cl. ...................... 435/197; 435/440; 536/23.2; 424/94.6
(58) Field of Search ................................ 435/197, 440; 536/23.2; 424/94.6

(56) References Cited

U.S. PATENT DOCUMENTS

| | | | |
|---|---|---|---|
| 4,215,759 A | 8/1980 | Diaz | ........................... 180/168 |
| 5,165,064 A | 11/1992 | Mattaboni | .................... 356/152 |
| 5,682,313 A | 10/1997 | Edlund et al. | ......... 364/999.999 |

FOREIGN PATENT DOCUMENTS

| | | |
|---|---|---|
| EP | 0 278 853 A1 | 8/1988 |
| EP | 0 774 702 A2 | 5/1997 |
| JP | 04-205007 | 7/1992 |
| WO | WO 99/59042 | 11/1999 |
| WO | WO 00/24911 | * 5/2000 |

OTHER PUBLICATIONS

Kusunoki et al. EMBL database—Accession #X51529. 1992.*

Emmanuel Valentin et al, "Cloning and Recombinant Expression of a Novel Mouse–secreted Phospholipase A$_2$", The Journal of Biological Chemistry, vol. 274, No. 27, 1999, pp. 19152–19160.

Jeffrey J. Seilhamer et al, "Cloning and Recombinant Expression of Phospholipase A$_2$ Present in Rheumatoid Arthritic Synovial Fluid", The Journal of Biological Chemistry, vol. 264, No. 10, 1989, pp. 5335–5338.

(List continued on next page.)

*Primary Examiner*—Ponnathapu Achutamurthy
*Assistant Examiner*—Yong Pak
(74) *Attorney, Agent, or Firm*—Oblon, Spivak, McClelland, Maier & Neustadt, P.C.

(57) ABSTRACT

This invention relates to a gene encoding human secretory type phospholipase A$_2$ (PLA$_2$). According to the invention, an expression vector having this gene, and a transformant having the expression vector are obtainable. The PLA$_2$ protein can be produced by the culture of the transformant.

16 Claims, 3 Drawing Sheets

OTHER PUBLICATIONS

Ruth M. Kramer et al, "Structure and Properties of a Human Non–pancreatic Phospholipase $A_2$", The Journal of Biological Chemistry, vol. 264, No. 10, 1989, pp. 5768–5775.

Ju Chen et al, "Cloning and Recombinant Expression of a Novel Human Low Molecular Weight $Ca^{2+}$–dependent Phospholipase $A_2$", The Journal of Biological Chemistry, vol. 269, No. 4, 1994, pp. 2365–2368.

Lionel Cupillard et al, "Cloning, Chromosomal Mapping, and Expression of a Novel Human Secretory Phospholipase $A_2$", The Journal of Biological Chemistry, vol. 272, No. 25, 1997, pp. 15745–15752.

Edward A. Dennis, "Diversity of Group Types, Regulation, and Function of Phospholipase $A_2$", The Journal of Biological Chemistry, vol. 269, No. 18, 1994, pp. 13057–13060.

Norihiko Kawamata et al, "Molecular analysis of the secretory phospholipase A2 gene, a candidate of Mom1 gene, in neuroblastomas", Cancer Letters 111 (1997) pp. 71–75.

Osamu Ohara et al, "JIKKEN IGAKU = Experimental Medicine", 1993, pp. 23–27.

Jun Ishizaki et al, "Cloning and Characterization of Novel Mouse and Human Secretory Phospholipase $A_2$s", The Journal of Biological Chemistry, vol. 274, No. 35, 1999, pp. 24973–24979.

A. E. Dennis et al, "The growing phospholipase $A_2$ superfamily of signal transduction enzymes", 1997, pp. 1–2.

* cited by examiner

HUMAN SECRETORY TYPE PHOSPHOLIPASE A₂

TECHNICAL FIELD

This invention relates to a human secretory type phospholipase $A_2$; a DNA encoding this protein; a vector having the DNA; a transformant having the vector; a method for producing the protein by using the transformant; an antibody recognizing the protein; a screening method for a compound by using the protein; and a compound obtained by the screening method.

BACKGROUND ART

Phospholipase $A_2$ ($PLA_2$; EC 3.1.1.4) is a general term of phospholipids-cleaving enzymes that hydrolyze the 2-acyl ester bond of 3-sn-phosphoglyceride. $PLA_2$ is involved in the digestion of phospholipids in food and the generation and metabolism of phospholipids in the cell membranes. In addition, $PLA_2$ plays as a rate-limiting enzyme of the arachidonic acid cascade in the production of lipid mediators including prostaglandins. It has been known that various types of $PLA_2$s exist in mammals. $PLA_2$s are classified into 4 different families, such as the secretory $PLA_2$, cytosolic $PLA_2$, $Ca^{2+}$-independent $PLA_2$, and platelet-activating factor-acetylhydrolase, based on the localization, $Ca^{2+}$ requirement, and substrate specificity (Balsinde et al., J. Biol. Chem. 272, 16069–16072 (1997)).

Among them, secretory $PLA_2$ family comprises $PLA_2$ enzymes that are secreted into the outside of the cells and have a relatively low molecular weight (13,000–15,000). As the member of the family, 5 types including IB type, IIA type, IIC type, V type, and X type, have been already identified. Each molecule has 12 to 16 Cys residues that form disulfide-bonds in the molecule, and possesses a consensus active site consisting of His-Asp residues. In addition, the molecules have a common $Ca^{2+}$ binding region. Micro mole order of $Ca^{2+}$ concentration is required for the exertion of the enzyme activity (Tischfield et al., J. Biol. Chem., 272, 17247–17250 (1997), Cupillard et al., J. Biol. Chem., 272, 15745–15752 (1997)).

It is assumed that IB type has a function as a digestive enzyme in the pancreas etc. and is involved in the progression of inflammation, such as endotoxin shock, through the binding to its specific receptor. It is also assumed that IIA type plays a role in various inflammatory responses because this type is expressed in blood platelets and synovial cells etc., and its expression is elevated during stimulation of inflammatory cytokines. However, the inflammatory response is normal in genetically IIA-deficient mice. Thus, its pathological significance remains unresolved. V type is expressed in the heart and several inflammatory cells. X type is expressed in the tissues related to the immunity such as spleen and thymus. Although it is suggested that both types are involved in the bio-regulation and inflammatory response, their importance in the body is not clearly identified (Hanasaki et al., Cell Technology, 17, 694–701 (1998)).

DISCLOSURE OF INVENTION

The object of this invention is to provide a novel type of human secretory phospholipase $A_2$; a DNA encoding the protein of this invention; a vector comprising the DNA of this invention; a transformant having the vector of this invention; a method for producing human secretory type phospholipase $A_2$ by using the transformant of this invention; an antibody specifically recognizing the protein of this invention; a screening method of a compound by using the protein of this invention; and a compound obtained form the screening method.

In the process of intensive studies regarding the physiological function of mouse X type $PLA_2$, the inventors found the presence of partial sequence with homology to mouse X type $PLA_2$ in Expressed Sequence Tags (EST) database. Based on the partial sequence, they found a DNA sequence encoding novel secretory type $PLA_2$ protein from mouse spleen cDNA library. Further, the inventors found out a DNA sequence encoding human secretory type $PLA_2$ protein (IID type) from human spleen cDNA library, to accomplish this invention.

The invention relates to:

A protein which comprises an amino acid sequence from First Gly to 125$^{th}$ Cys of that shown in SEQ ID No.:27;

The protein as described above which comprises an amino acid sequence from −20th Met to 125th Cys of that shown in SEQ ID No.:27;

A protein which comprises the above described amino acid sequence, in which one or more amino acid residues are substituted, deleted, inserted, or added, and has a secretory type phospholipase $A_2$ activity;

A DNA which encodes the protein as described above;

The DNA as described above which comprises a base sequence from 89th A to 463rd C of that shown in SEQ ID No.:26;

The DNA as described above which comprises a base sequence from 29th to 463rd C of that shown in SEQ ID No.26;

A DNA which hybridizes to the DNA as described above under the stringent condition and encodes the protein having a secretory type phospholipase $A_2$ activity;

A vector which has the DNA as described above;

A transformant which is obtained by inserting the expression vector as described above to a host;

The transformant as described above wherein the host is a mammalian cell line;

A method for producing recombinant secretory type phospholipase $A_2$ which comprises a step for culturing the transformant as described above and a step of recovering a produced recombinant protein from the culture;

An antibody which specifically recognizes the protein as described above;

A diagnostic agent for secretory type phospholipase $A_2$-related diseases, which comprises the antibody as described above;

An assay kit for secretory type phospholipase $A_2$, which comprises the antibody as described above;

A therapeutic agent for secretory type phospholipase $A_2$-related diseases, which comprises the antibody as described above;

A screening method of a compound specifically inhibiting a secretory type phospholipase $A_2$ activity which uses the protein as described above; and A compound which is obtained by the screening method as described above.

The protein of this invention is "A protein which comprises an amino acid sequence from first Gly to 125th Cys of that shown in SEQ ID No.:27". Preferable is "A protein which comprises an amino acid sequence from −20th Met to 125th Cys of that shown in SEQ ID No.:27". "A protein which comprises an amino acid sequence from first Gly to 125th Cys of that shown in SEQ ID No.:27" means a mature protein. "A protein which comprises an amino acid sequence from −20th Met to 125th Cys of that shown in SEQ ID No.:27" is an immature protein that has a signal peptide. The protein of this invention also includes "A protein which comprises the amino acid sequence as described above, in which one or more amino acid residues are substituted, deleted, inserted, or added, and has a secretory type phospholipase $A_2$ activity". Number or site of "substitution, deletion, insertion, addition of amino acid residue" is not limited, if the modified protein has the same activity as the protein consisting of the amino acid sequence shown in SEQ ID No.:27. In this invention, "phospholipase $A_2$ activity" means "phospholipid-cleaving activity that hydrolyzes 2-acyl ester bond of 3-sn-phosphoglyceride in a $Ca^{2+}$-dependent manner".

Although these mutations in the amino acid sequences can be caused naturally by mutation or modification after transcription, artificial modification can also be caused by the DNA of this invention. The protein of this invention includes all proteins which are encoded by modified DNA have the characteristics as mentioned above regardless of the cause or mean of these modification/mutation.

The DNA of this invention means "a DNA encoding the protein of this invention". As the DNA of this invention, a DNA encodes the mature protein and comprises a base sequence from 89th G to 463rd C of that shown in SEQ ID No.:26 is preferably given for example. More preferably, a DNA encodes the immature protein and comprises a base sequence from 29th A to 463rd C of that shown in SEQ ID No.:26 is given for example. A DNA that hybridizes to the DNA of this invention under the stringent condition and encodes the protein having a secretory type phospholipase $A_2$ activity is also included in the DNA of this invention. "A DNA that hybridizes to the DNA of this invention under the stringent condition" can be obtained by using the DNA of the encoding region as a probe. "Hybridize under the stringent condition" means that positive hybridizing signal can be observed after heating at 42° C. in 6×SSC, 0.5% SDS and 50% formamide solution and washing 68° C. in 0.1×SSC, 0.5% SDS solution.

Using the DNA of this invention, a production of the recombinant protein can be performed based on textbooks and references such as Molecular Cloning etc. More concretely, a transcription initiation codon is added at upper stream of the DNA to be expressed, and a transcription stop codon is added at down stream of the DNA. A regulator gene such as a promoter sequence (Ex. Trp, lac, T7, SV40 initial promoter) which controls transcription is also added. The expression plasmid, which can replicate and work in the host cells, is prepared by insertion of the DNA into an appropriate vector (ex. PBR322, pUC19, pSV.SPORT1 etc.).

The transformant is obtained by insertion of the expression vector into host cells. As a host cell, procaryotes such as E. coli, monocellular eukaryotes such as yeast, and cells derived from multicellular organisms such as insects and mammals are given for examples. Mammal's cells are preferable. As a mammal's cell, CHO cell, 293 cell, COS-7 cell are given for example.

The antibody of this invention is an antibody against the polypeptide of this invention or peptide fragment that can compose the epitope, and includes both of polyclonal antibodies and monoclonal antibodies. Secretory type $PLA_2$ is involved in the release of fatty acids (ex. arachidonic acid). Excess release of fatty acids cause various diseases such as septic shock, adult respiratory distress syndrome, pancreatitis, bronchial asthma, allergic rhinitis, rheumatoid arthritis, etc. It is possible to diagnose these diseases by the evaluation of a concentration of secretory type phospholipase $A_2$. The antibody of this invention provides a diagnostic agent and an assay kit for secretory type phospholipase $A_2$-related diseases. If the antibody inhibits a $PLA_2$ activity, the antibody itself can be a therapeutic agent for the diseases caused by $PLA_2$.

BEST MODE FOR CARRYING OUT THE INVENTION

Figure 1:
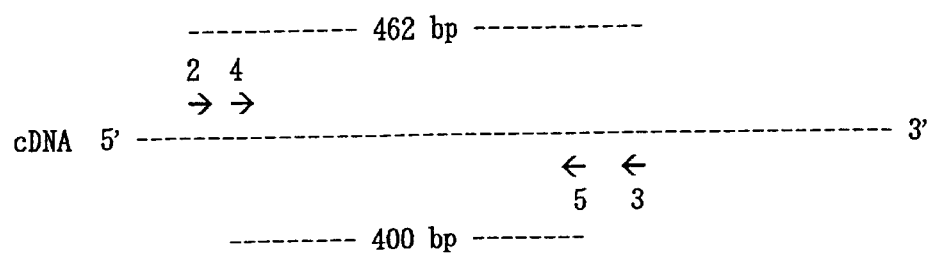
FIG. 1 shows a positional relationship of oligomers of SEQ ID No.:2, 3, 4, and 5.

This invention mainly relates to a novel human secretory type phospholipse $A_2$.

Explained below are a preparation method for the protein of this invention, a preparation method for the antibody, and a screening method for the compound which inhibits the phospholipase $A_2$ activity as below. Unless otherwise mentioned, for example, gene recombinant, production methods for a recombinant protein using animal cells, insect cells, yeast and E. coli, separation and purification methods for the expressed protein, analysis method, immunological means, technologies well-known in this field, can be used to this invention.

The DNA Sequence Encoding the Secretory Type $PLA_2$ of this Invention

The DNA of this invention can be produced or obtained based on the sequence information described in this invention by general gene engineering-technique (Molecular Cloning 2d Ed, Cold Spring Harbor Lab. Press (1989) so on). More specifically, cDNA library is prepared by conventional methods from appropriate sources expressing the DNA of this invention, and the DNA clone is selected from the library using specific probes or antibodies (Proc. Natl. Acad. Sci., USA., 78, 6613 (1981); Science, 22, 778 (1983) so on). Examples of the cDNA source are cells and tissues that express the DNA of this invention or cultured cells derived from these cells or tissues. Separation of total RNA, separation and purification of mRNA, obtaining cDNA and it's cloning can be performed by conventional methods. The commercially available cDNA libraries such as Clontech library can also be used.

The screening method for the DNA of this invention from the library is not limited, and can be performed by conventional methods. Available methods are as follows: an immunological screening for the corresponding cDNA clone using a specific antibody for the protein encoded by the cDNA, a plaque hybridization using a probe that selectively binds to the objective DNA, a colony hybridization and so on and combination of these methods. DNA Probes used in these methods are chemically synthesized based on the information of the DNA sequence or a fragment of the obtained DNA of this invention. Also sense/antisense primers designed from the information of the sequence can be used for cloning probes.

DNA/RNA amplification by PCR method (Science, 230, 1350 (1985)) can suitably be used for obtaining the DNA of this invention. If it is difficult to obtain the full length cDNA from the library, various methods such as RACE (Rapid amplification of cDNA ends;: Experimental Medicine, 12(6), 35 (1988)) can be supplemented. The primers used for the PCR method can be designed based on the sequence information of the DNA clarified by this invention. Such primers can be synthesized by conventional methods. Isolation and purification of the amplified DNA/RNA fragments can also be performed with conventional method descried above. For example, it can be performed by gel electrophoresis etc. The DNA or various fragments obtained at the above methods can be sequenced by dideoxy method (Proc. Natl. Acad. Sci., USA., 74, 5463 (1977)), Maxam and Gilbert method (Methods in Enzymology, 65, 499 (1980)) or by using a sequencing kit etc.

Hereafter, the DNA cloning method of this invention is described.

(1) Sequence determination of the DNA encoding the mouse secretory type $PLA_2$

A sequence determination method for the DNA fragment encoding mouse secretory type $PLA_2$ which corresponds to human secretory type PLA2 of this invention is described below. Finding out a sequence homologous to mouse X type PLA2 is firstly done. Next step is preparing primers on the basis of the sequence. And finally, PCR is performed using cDNA library originated mouse spleen as a template. By sequencing the obtained DNA fragment, the DNA fragment encoding mouse secretory type $PLA_2$ can be determined.

(A) Isolation of a novel $PLA_2$ cDNA fragment and analysis of expression pattern in mouse tissues In order to analyze the gene from which a DNA fragment is originated and function of a protein encoded by the gene, it is necessary to isolate cDNAs which connect to 5' terminus and 3' terminus of this fragment and to confirm the sequence integrity. For this purpose, it is advantageous to use tissues with high expression level of the gene.

The existence of the expression and its level among tissues can be analyzed by a hybridization with radio-labeled DNA fragment (probe) with mRNAs extracted from each tissue immobilized on a sheet (Northern hybridization). It is necessary to obtain a $PLA_2$ cDNA fragment used as a probe for comparing the quantities in mouse tissues. Such a fragment can be isolated by PCR using primers prepared based on the sequence of EST database and using a cDNA sample originated from mouse tissues as a template. The northern analysis was performed by the obtained cDNA fragment (SEQ ID No.:1). The result indicated clearly that the gene is highly expressed in mouse spleen (B) Isolation of full length cDNA encoding mouse secretory type $PLA_2$ For example, upper stream sequence including 5' terminus of the cDNA and down stream sequence including 3' terminus of the cDNA can be obtained by PCR with so called RACE method: Rapid Amplification of cDNA End. Oligomer pairs used in the PCR consist of one PLA2-specific primer, and the other that corresponds to adapter sequence which is added on the 5' and 3' end of the cDNA. Marathon-ready cDNA (Clontech) originated mouse spleen can be used as a cDNA sample. DNA sequence having mouse secretory type $PLA_2$ gene and the amino acids sequence encoded by the gene obtained by the method are shown in SEQ ID No.:13 and 14, respectively.

(C) Isolation of full length cDNA encoding human secretory type $PLA_2$

Generally, it is expected that the same gene have high sequence homology between mouse and human. It is expected that the amino acids residues conserved in $PLA_2s$ originated from various animals (consensus sequence) of which primary structure has been determined are also conserved in the novel $PLA_2$. Therefore, the cDNA sequence corresponding to the consensus sequence would have high homology with cDNA of human type $PLA_2$ and this region will be useful for the cloning of human homolog based on the mouse PLA2 sequence information. Furthermore, the mouse cDNA sequence of this invention has high homology with IIA type. It can be predicted that the human secretory type $PLA_2$ gene of this invention also has high homology with IIA type. Based on the above assumption, the oligomers were designed by the consensus sequence conserved in these $PLA_2$ and partial sequence corresponding to human secretory type $PLA_2$ was cloned by PCR using human genomic DNA (Boehringer Mannheim) as a template. For example, upper stream sequence including 5' terminus of the cDNA and down stream sequence including 3' terminus of the cDNA can be obtained by PCR with RACE method described above. The oligomer pairs used in the PCR consist of one $PLA_2$-specific primer, and the other corresponds to adapter sequence which is added on the 5' and 3' end of the cDNA. Or it can be obtained by PCR using human cDNA library as a template based on mouse PLA2 cDNA sequence which can be expected to have high homology with human counterpart. Marathon-ready cDNA of human small intestine which is expected to express highly was used as a template. DNA sequence having human secretory type $PLA_2$ gene and the amino acids sequence encoded by the gene obtained by the method are shown in SEQ ID No.:26 and 27, respectively.

Preparation of the Protein of this Invention (1)Expression of a recombinant type $PLA_2$ protein The protein of this invention can be obtained as a recombinant protein by genetic engineering means (Science, 224, 1431 (1984); Biochem. Biophys. Res. Comm., 130, 692 (1985); Proc. Natl. Acad. Sci., USA., 80, 5990 (1983) etc.). More specifically, a gene encoding a desired protein is inserted into an appropriate vector. A transformant is obtained by incorporating the vector into host cells. A recombinant protein can be obtained by the culture of the transformant.

Both eucaryote and procaryote can be used as host cells. The eucaryote's cells include cells of vertebrate and yeast etc. COS cell (Cell, 23, 175 (1981)) of ape and ovarian cell of a Chinese hamster so on are used as the vertebrate cells.

An expression vector which has a promoter located in upper stream of the gene aimed for expression, splice junction of RNA, polyadenylation region and transcription end sequence so on can be used. And the vector may have a replication origin if it is necessary. As an example for the expression vector is pSV2dhfr (Mol. Cell. Biol., 1, 854 (1981)) having SV40 early promoter etc. As a eucaryotic microorganism, yeast, especially Saccharomyces yeast, is widely used. pAM82(Proc. Natl. Acad. Sci., USA., 80, 1 (1983)) having promoter for acid phosphatase gene etc. can be used as the expression vector for yeast.

As a host of a procaryote, *E. coli* or *Bacillus subtilis* are widely used. If these cells are used as a host, it is preferable to use plasmid vector which is replicable in the host and contains a promoter for expression of an objective gene at upper stream of the gene, SD sequence, initiation codon necessary for starting protein synthesis. As a host, *E. coli* K12 strain etc. is used. As a vector, generally pBR322 and it's derivative are used. It is not limited to these host/vector system. Various kinds of known strains and vectors can also be used. As a promoter, trp promoter, lpp promoter, lac promoter, PL/PR promoter, etc. can be used.

As an insertion method of a desired recombinant DNA into host cell and a transformation method, various general methods are employable. The obtained transformant can be cultured according to general methods and the desired protein can be produced by the culture. As a medium used for the culture, appropriate medium can be selected from various kinds of commonly used medium according to a host cells. For example, the transformant can be prepared by an insertion of the vector comprising human secretory type $PLA_2$ gene of this invention at down stream of pSVL SV late promoter and the recombinant secretory type $PLA_2$ protein can be produced by a culture of the transformant at 37° C. for 3 days under the existence of 5% $CO_2$.

The recombinant protein can be separated and purified by various separating procedures utilizing its physical and chemical characteristics, etc. (Biochemistry, 25(25), 8274 (1986); Eur. J. Biochem., 163, 313 (1987) etc.). For such separating method, extraction by salt, centrifugation, osmotic shock method, ultrasonication, ultrafiltration, gel filtration, various kinds of liquid chromatography such as adsorption chromatography, ion exchange chromatography, affinity chromatography, or high performance liquid chromatography, dialysis, and combination of these method are applicable examples.

(2) Preparation of variant

Amino acid sequence can be changed with deletion/insertion at any position. The methods known as protein engineering can be widely applicable to the substitution of the amino acids sequence. Site-directed deletion method (Nucl. Acids Res., 11, 1645, (1983)), Site-specific mutagenesis method (Zoller, M. J. et al., Methods in Enzymol., 100, 468, (1983), Kunkel. T. A. et al., Methods in Enzymol., 154, 367–382, (1987)), PCR mutation method, method using restriction enzyme and synthesized gene, etc. are the applicable examples.

Using site-specific mutagenesis inducing method described in Sambrook, J. et al., Molecular Cloning: A Laboratory Manual 2nd, No.1–3, Cold Spring Harber Laboratory Press publication New York (1989) or PCR method as a Site-specific mutagenesis method, mutations can be introduced into the DNA sequence of this invention.

By using appropriate vector and host strain, the DNA sequence mutated by these methods can be expressed with genetic engineering method described such as in Sambrook, J. et al., Molecular Cloning: A Laboratory Manual 2nd, No.1–3, Cold Spring Harber Laboratory Press publication New York (1989). Several kits such as Mutan™-SuperExpress Km Mutan™-K (Takara shuzo), Quick Change Site-Directed Mutagenesis Kit (Stratagene) can be used.

Generally, site-specific mutagenesis method can be performed by obtaining a single strand vector including the sequence encoding the protein. Oligo nucleotide primer with.desired mutation in the sequence can be produced by general synthesis method, such Crea's method (Crea, R. et al., Proc. Natl. Acsd. Sci. U.S.A., 75, 5765, 1978). Annealing of this primer with the single strand vector having this DNA sequence is performed, then reaction with DNA polymerase such as *E. coli* polymerase I Klenow flagment is followed to complete the synthesis of the mutated strand. Hetero double strands comprising one strand encoding non-mutation sequence and another strand having desired mutation are formed. Appropriate bacteria or cells are transformed by this double strand vector. The clone is selected by hybridization of radioactivity probe consisted of $^{32}$P-labeled mutated sequence-including primer (Wallace, R. B., Nucleic Acids Res., 9, 3647, 1981). Selected clone contains the recombinant vector having mutated sequence. After the selection of such clone, the region encoding mutated protein can be inserted into an expression vector for transformation.

Hereafter, variants can be produced by the host cells according to the preparation method of the recombinant protein shown in (1).

Determination of Secretory Type $PLA_2$ Activities

The determination of $PLA_2$ activities of the recombinants and the variants obtained above was carried out by the following method.

① React the culture products containing recombinant secretory type $PLA_2$ protein or the control culture products containing no recombinant secretory type $PLA_2$ protein with $^3$H-oleic acid-labeled *E. coli* membrane phospholipid fractions.

② Determine the quantity of released $^3$H-oleic acid according to Elsbach's method (Methods Enzymol., 197, 24–31 (1991)).

③ Certify the existence of $PLA_2$ activity by comparing the quantity of $^3$H-oleic acid.

Preparation of Antibody Against the protein of this Invention

The antibody against the protein of this invention can be produced by the following methods.

(1) Preparation of polyclonal antibody

Peptides synthesized by a usual peptide synthesizer based on a part of the deduced amino acids sequence are used as immunogen. Alternatively, protein produced by bacteria, yeast, insect cells and mammalian cells, which are transformed by the expressing vector encoding the protein into, can be purified by general protein chemical method and also used as immunogen. Thus, the polyclonal antibody that specifically recognizes the protein can be easily prepared and purified. Using this immunogen, animals are immunized according to the appropriate method described in Antibodies; A Laboratory Manual, Lane, H. D. et al., Cold Spring Harber Laboratory Press publication New York 1989. For example, polyclonal antibody is prepared from the serum of the immunized animals, such as mouse, rat, hamster, and rabbit.

(2) Monoclonal antibody

Lymphocytes are isolated from spleen or lymph node of the immunized mouse or rat with the immunogen as described above. Hybridomas are prepared by fusion of the isolated lymphocyte and myeloma cells according to Kohler and Milstein's method (Nature, 256, 495–497(1975)). Monoclonal antibody can be produced from the hybridoma. For example, the monoclonal antibody against the protein of this invention can be obtained by the following steps:

(a) Immunization of mice by the protein, (b) Isolation of immunized mouse spleen and separation of the spleen cells, (c) Fusion of separated spleen cells and mouse myeloma cells in the presence of fusion-promoting agent, such as polyethylene glycol, according to Kohler's method described above, (d) Culture of hybridoma cells obtained from selective medium in which unfused myeloma cells can not grow, (e) Selection of hybridoma cells that produce the desired antibody by the evaluation with enzyme-linked immunosorbent assay (ELISA), and western blot, and cloning them by the limited-dilution method etc., (f) Culture of the hybridoma cells that produce the monoclonal antibody and collection of the monoclonal antibody.

Assay Kit for Secretory Type $PLA_2$ and Diagnostic Reagent for Secretory Type $PLA_2$ Relating Disease In this invention, the protein of this invention can be assayed by using the monoclonal antibody against the protein. Any kind of assay using the antibody against the protein of this invention is applicable, if the assay determines the quantity of antibody corresponding to the antigen quantity (ex. Quantity of the protein of this invention) in the assay solution, or the quantity of antibody-antigen complex by the chemical or physical methods, and calculates them by the standard curve prepared by using the standard solution containing a known quantity of the antigen. For examples, nephelometry, competition method, immunometric assay, and sandwich method can be adapted.

For the immobilization of the antigen or the antibody, the chemical binding generally useful for immobilization of the protein or enzyme can be used. As a carrier, insoluble polysaccharides such as agarose, dextran, or cellulose, or synthetic resins such as polystyrene, polyacrylamide, silicon, or glass are given for examples.

In the sandwich method, the quantity of the protein in assay solution can be determined by the following steps.

(1) React the immobilized antibody of this invention with the assay solution, then react them with another labeled-antibody of this invention.

(2) Determine the activity of the labeling agent on the immobilized carrier.

There is no need that the immobilized antibody is the same as the labeled antibody. For example, if the immobilized antibody recognizes the N-terminus of the protein, the labeled-antibody that recognizes C-terminus of the protein can be used.

Radioisotope, enzyme, and fluorescent substance can be used as a labeling agent. As a radioisotope, $^{125}I$, $^{3}H$, $^{14}C$ etc. can be used. As an enzyme, peroxydase, β-galactosidase, β-glucosidase, alkaline phosphatase, etc., can be used.

By using these assay, if the concentration of the protein is excess, it is possible to diagnose or diagnose patients with the diseases such as septic shock, adult respiratory distress syndrome, pancreatitis, external injuries, bronchial asthma, allergic rhinitis, rheumatoid arthritis, etc.

Therefore, the antibody of this invention provides "Diagnostic reagent" and "Assay kit" which can be useful in the diagnosis of these diseases.

Screening Method for a Compound that Specifically Inhibits $PLA_2$ Activity

As a "Screening method" of this invention, high through put screening with the protein of this invention is given for example. For example, samples, phospholipid substrate (racemic diheptanoyl thio-phosphatidylcholine) and color-developing reagent (5,5'-dithiobis (2-nitrobenzoic acid)) are added into 96-well plate according to the Reynolds's method (Anal. Biochem. 204, 190–197(1992)). After the addition of the protein, the wells were incubated at 40° C. for the appropriate time, and the change of absorbance (OD at 405 nm) is measured. The inhibiting activity of the sample for this secretory type $PLA_2$ can be evaluated by comparing with the value obtained in the absence of the sample.

Compound Obtained from the Screening Method

Secretory type $PLA_2$ is involved in the release of fatty acids (ex. arachidonic acid). Excess release of fatty acid causes various diseases such as septic shock, adult respiratory distress syndrome, pancreatitis, external injuries, bronchial asthma, allergic rhinitis, rheumatoid arthritis. The compound obtained from the screening method inhibits the activity of secretory type $PLA_2$. Therefore, the compound is useful for the therapy of diseases including septic shock in which the excess production of secretory type $PLA_2$ is involved.

The compound includes pharmaceutically acceptable salts. The salt is prepared by well-known methods. Non-toxicity alkaline metal salt, such as sodium, potassium, litium, calcium, magnesium, and barium, alkali earth metal salt, and ammonium salt, etc. are included.

A pharmaceutical preparation is made with a pharmacologically effective quantity of the compound as an active ingredient. As a medication unit form of the pharmaceutical preparation, various kinds of form can be selected according to an object of therapy. As a solid dosage form, tablet, pill, powder, epipastic, granule, capsule, etc. are included. And as a liquid dosage form, solution, suspension, emulsion, syrupus, elixir, etc. are included. These are classified into oral agent, non-oral agent, nasal agent, vaginal agent, suppository, sublingual agent, ointment, etc. according to the dosage route. Preparation and molding can be performed according to the general methods.

The dosage forms of the pharmaceutical preparation as described above are not limited and these are determined according to each preparation form, age of subjects, sex, state of a disease or other condition. For example, tablet, pill, granule, capsule, solution, suspension, and emulsion are given through oral. An injection agent is used by itself or as the mixture with a general fluid replacement such as dextrose or amino acids, and given through vein. Moreover, injection is given into muscle, skin, abdominal cavity or under skin, if necessary.

The effective quantity of the invention compound should be comprised in the pharmaceutical preparation as mentioned above and its dosage is not limited. It is chosen according to the effect of desired therapy, the dosage method, the duration of therapy, the age of subject, sex, and the other conditions. Generally, the dosage is about 1–10 mg per 1 kg body weight a day. The preparations can be given in one to several divisions per day.

The antibody of this invention inhibits the $PLA_2$ activity of the secretory type PLA2 of this invention via the specific binding to PLA2 of this invention. Therefore, the antibody of this invention, as well as the compound obtained from the screening method of this invention, are useful for the therapy of diseases, such as septic shock, in which excess production of secretory type $PLA_2$ is involved.

EXAMPLE

The invention is explained in more detail by the following examples.

General experiment protocols used in each step in this invention follow Current Protocols in Microcular Biology (F. M. Ausubel et al. Ed., John Wiley & Sons. Inc.). DNA oligomers are purchased from International Reagents Corp. (Kobe, Japan). Data analysis was performed with GENETYX-SV/RC of Software Development Inc. (Japan). Determination of DNA sequences was routinely performed with several clones in order to eliminate the effects of misincorporation that might be caused in the PCR reactions.

cDNA fragment that can encode the $PLA_2$ detected in EST database is shown as SEQ ID No.:1 at Sequence Listing. This sequence is a fragment. It is required to isolate the undetected cDNAs connected with 5' terminus and 3' terminus of the fragment and to reconfirm the fragment sequence at the same time for the analysis of the fragment-originated gene itself and the function of the protein encoded by the gene. For the cloning the full length cDNA, it is favorable to use the tissues in which the gene is highly expressed. In order to compare the quantities of the gene expression levels among the mouse tissues by Northern analysis, it is required to obtain a $PLA_2$ cDNA fragment available for the probe. Such $PLA_2$ cDNA fragment can be isolated by PCR using cDNA samples derived from mouse tissues as templates.

Example 1

Isolation of a cDNA Fragment of a Novel Mouse $PLA_2$

Short DNA oligomers shown in SEQ ID No.:2 to 5 were prepared based on the DNA sequence shown in SEQ ID No.:1. A relative positioning of these DNA oligomers are shown in FIG. 1. 462 base pairs of $PLA_2$ cDNA fragments could be amplified by PCR using the oligomer pair of SEQ ID No.:2 and 3, and 400 base pairs of $PLA_2$ cDNA fragments could be amplified by PCR using oligomers of the SEQ ID No.:4 and 5. If PCR was performed by using oligomers of SEQ ID No.2 and 3 at first, then amplified products were used as templates at second PCR with oligomers of SEQ ID No.4 and 5, it was expected that $PLA_2$ cDNA could be amplified with higher specificity and sensitivity (Nested-PCR).

cDNA samples were prepared from reverse transcription of mRNA extracted from mouse tissues (brain, heart, kidney, spleen, stomach, etc.) of 129/Svj strain. Using these cDNA samples as templates, PCR was performed using oligomers of SEQ ID No.:2 and 3. TaKaRa Ex Taq (Takara Shuzo, Japan) was used as an enzyme, and composition for PCR reaction was followed to the instruction of the enzyme. As an amplification device, Thermal Cycler (Perkin Elmer Cetus) was used. The amplification was performed at 94° C. for 1 min, 55° C. for 1 min, and 72° C. for 3 min for 30 cycles. After the reaction was completed, second PCR was performed using 1 µl of the reaction solution as template with oligomers of SEQ ID No.:4 and 5. The reaction condition was same as the first PCR. The solution of the PCR reaction was applied to 1.2% agarose gel electrophoresis and the amplified products were separated. The DNA of the expected size was amplified from the cDNA originated with all tissues.

The DNA was cut out from the gel. Purification of DNA was performed using GenElute Agarose spin column (spelco). The DNA was ligated with CRII vector (Invitrogen), and *E. coli* SURE strain (Stratagene) was transformed with the ligation solution. The obtained recombinant *E. coli* was cultured, and plasmid DNA was prepared by GFX Micro Plasmid Prep Kit (Pharmacia Biotech). The sequence inserted into the vector was determined with PRISM 310 Genetic Analyzer (PE Applied Biosystems). The result indicated that the DNA consisted of the sequence corresponding to SEQ ID No.:1 was amplified by the PCR.

Example 2

Analysis of Expression Pattern of the Secretory Type $PLA_2$ mRNA in Each Mouse Tissues The existence and its level of the expression in tissues can be analyzed by a hybridization with radio-labeled DNA fragment (probe) with mRNAs extracted from each tissue immobilized on a sheet (Northern hybridization). The purified DNA fragment after the PCR amplification was labeled with Prime-It II (Stratagene). Using this fragment as a probe, the hybridization was performed with mouse Multiple tissue northern blot (Clontech). Autoradiography was performed after the washing with the solution containing appropriate concentration of salt. The result indicated that the PLA2 mRNA was highly expressed in spleen among the tissues examined, and the existence of two types of mRNAs consisting of 1.2 kb and 2.4 kb.

Example 3

Determination of cDNA Primary Construction of Mouse Secretory Type $PLA_2$

Up stream including 5' terminus and down stream including 3' terminus of the cDNA can be isolated by the following method utilizing the information of known portion (central part) of the cDNA. Several antisense oligomers and sense oligomers are prepared according to the known sequence. cDNA including unidentified part can be amplified using cDNA samples which has attached adapter DNAs at the end of cDNA. Oligomer pairs consisted of a oligomer corresponding to the adapter-specific sequence and a PLA2 specific oligomer are used.

Mouse spleen Marathon-ready cDNA (Clontech) was used as a cDNA sample. Oligomers used for the RACE method were shown in SEQ ID NO.:6 to 10. Among them, SEQ ID No.:6, 7, and 8 are antisense oligomers for isolating 5' up stream, and SEQ ID No.:9 and 10 are sense oligomers for isolating down stream.

RACE method was performed by Nested PCR as same as PCR amplification of the central portion. For 5' side RACE, the oligomer of SEQ ID No.:6 and oligomer AP-1 attached with RACE kit (Clontech) were used at the first RACE, and the oligomer of SEQ ID No.:7 and oligomer AP-2 (Clontech) were used at the second RACE. For 3' side RACE, the oligomer of SEQ ID No.:9 and AP-1 were used at the first RACE, and the oligomer of SEQ ID No.:10 and AP-2 were used at the second RACE. TaKaRa Ex Taq (Takara Shuzo, Japan) was used as an enzyme. The first amplification was performed at 94° C. for 1 min, 60° C. for 1 min, and 72° C. for 2 min for 30 cycles, the second amplification was performed at 94° C., for 1 min, 62° C. for 1 min, and 72° C. for 2 min for 30 cycles. After the PCR, the amplified products were separated by electrophoresis. A band of about 220 base pair was detected by 5'RACE and a band about 950 base pair was also detected by 3' RACE. The cloning of these DNAs were performed as the same way of Example 1 and the sequences were determined.

A new antisense oligomer (SEQ ID NO.:8) was prepared for 5' side RACE from the sequences determined in the process so far. The PCR was performed by using SEQ ID No.:8 oligomer instead of the SEQ ID No.:7 oligomer at the second nested-PCR, and the clone including upper region was obtained.

Three parts of $PLA_2$ cDNA were isolated separately. Those are upper region, central part, and down-stream region. To confirm that these cDNAs are derived from one integral gene, oligomers shown at SEQ ID NO.:11 and 12 were prepared and the PCR was performed using Marathon-ready cDNA (Mouse spleen, Clontech) as a template. Native Pfu polymerase (Stratagene) was used as an enzyme. The amplification was performed at 94° C. for 1 min, 60° C. for 1 min, 72° C. for 4 min for 30 cycles. The amplified DNA was cloned as same as described above, and the sequence was determined. The determined cDNA sequence is shown at SEQ ID No.:13 and the amino acids sequence encoded by the cDNA is shown at SEQ ID No.:14.

From the length of the cDNA encoding the protein, it is clear that the number of amino acid residues of the PLA2 protein is 145. This protein possesses all structural features (central part for $PLA_2$ activity, sequence of $Ca^{2+}$ binding part, number of Cys residues) conserved among the secretory type $PLA_2$ family molecules. However, this protein consists of a different sequence from any of known secretory type $PLA_2$s, and homology at the amino acids level are 40.0% with mouse IB type, 46.3% with mouse IIA type, 40.0% with mouse IIC type, 41.4% with mouse V type, and 37.6% with mouse X Type, respectively.

Example 4

Determination of cDNA Primary Construction of Human Secretory Type $PLA_2$

Generally, it can be expected that same gene of mouse and human have high sequence homology each other. Therefore, it was expected that the completely conserved amino acid residues (consensus sequence) of which primary structures are known from various animals are conserved in the novel $PLA_2$. From these insights, it was considered that the cDNA sequence corresponding to the consensus sequence in mouse cDNA sequence determined at Example 3 would have high homology to human $PLA_2$ and this region is useful for the cloning of human homolog based on the mouse $PLA_2$ gene information. Four oligomers were designed on basis of the above-mentioned assumption.

Two oligomers of SEQ ID No.:17 and 18 were prepared on the basis of cDNA sequences corresponding to 40th Thr to 46th Lys and 47th His to 53rd His shown in SEQ ID No.:13. And oligomers (SEQ ID No.:19 and 20) were also prepared on the basis of cDNA sequence corresponding to 83th Trp to 89th Cys and 79th Asp to 85th Glu shown in SEQ ID No.:13. The human $PLA_2$ that has high homology to mouse $PLA_2$ was isolated with high sensitivity and high specificity by Nested-PCR as described in Example 1 using these oligomers. First PCR was performed using oligomers of SEQ ID No.17 and 19. Using the amplified products as templates, second PCR was performed with oligomers SEQ ID No.:18 and 20. The first and second PCR were performed at 94° C. for 1 min, at 45° C. for 1 min, at 72° C. for 3 min for 30 cycles and the other condition was as same as Example 1. Marathon-ready PCR cDNA (Human spleen, Clontech) was used for the first PCR as a template. The amplified product consisted of about 120 base pairs detected after the electrophoresis.

cDNA fragment of 117 base pairs would be amplified by two rounds of PCR, if the amplified products were mouse $PLA_2$ based on the mouse sequence. Therefore, it was expected that the product obtained by using the human cDNA as a template would be a novel cDNA fragment of human $PLA_2$. This fragment was cloned as same as Example 1 and the sequence of the fragment was determined. The sequence (76 base pairs originated from human cDNA sample located between the oligomers of SEQ ID No.:18 and 20) is shown in SEQ ID No.:21. This fragment was expected to be a part (central part) of novel human $PLA_2$ cDNA, because this fragment has 71% homology to the corresponding region of mouse $PLA_2$ cDNA, and an amino acid sequence encoded by this fragment has characteristic residues of secretory type $PLA_2$.

cDNA of the upper stream including 5' terminus and the down stream including 3' terminus were isolated by RACE method. The experiment was conducted on the condition described in Example 3 and Marathon-ready PCR cDNA (Human spleen, Clontech) was used as a template. Two antisense oligomer sequences for isolating upper stream and two sense oligomer sequences for isolating down stream are shown in SEQ ID No.:22 to 25. After the RACE, DNA fragments of about 350 base pairs at 5' side and about 600 base pairs at 3' side were obtained and the sequence was determined. The central part, the 5' part, and the 3' part have continuity and the connected sequence is shown at SEQ ID No.:26.

From the length of the cDNA encoding the protein, the number of amino acid residues of the PLA2 protein is 145. This protein (SEQ ID No.:27) conserves all structural features (central part of PLA2 activity, sequence for Ca2+ binding part, and number of Cys residues) conserved among secretory type $PLA_2$ family molecules. However, this protein consists of a different sequence from any of known secretory type $PLA_2$s, and homology of the amino acids sequence is 34.8% with human IB type, 47.6% with human IIA type, 40.7% with human V type, and 33.9% with human X type.

Example 5

Expression of the Recombinant $PLA_2$ Protein

PCR was performed by using the oligomers of SEQ ID No.:15 and 16 or SEQ ID No.:28 and 29, and using the cDNAs of mouse and human secretory type PLA2s as the templates, and the cDNA sequence encoding the region of the amino acids (the cording region) was amplified. The oligomers shown in SEQ ID No.:15 and 28 have a sequence recognized by the restriction enzyme NotI and a sequence (Kozak sequence) that promotes the transcription from mRNA to protein. The oligomers shown in SEQ ID No.:16 and 29 have a sequence recognized by the restriction enzyme XbaI. There is no sequence recognized by the restriction enzyme NotI or XbaI within the cording region. Therefore, after the digestion of PCR-amplified cDNA fragments with these restriction enzymes, the cDNA corresponding to the cording region can be prepared. It has the Kozak sequence at upper stream of the transcription starting point and the cutting edges of NotI or XbaI on the upper terminus and the down stream terminus of the cDNA, respectively.

Figure 2:
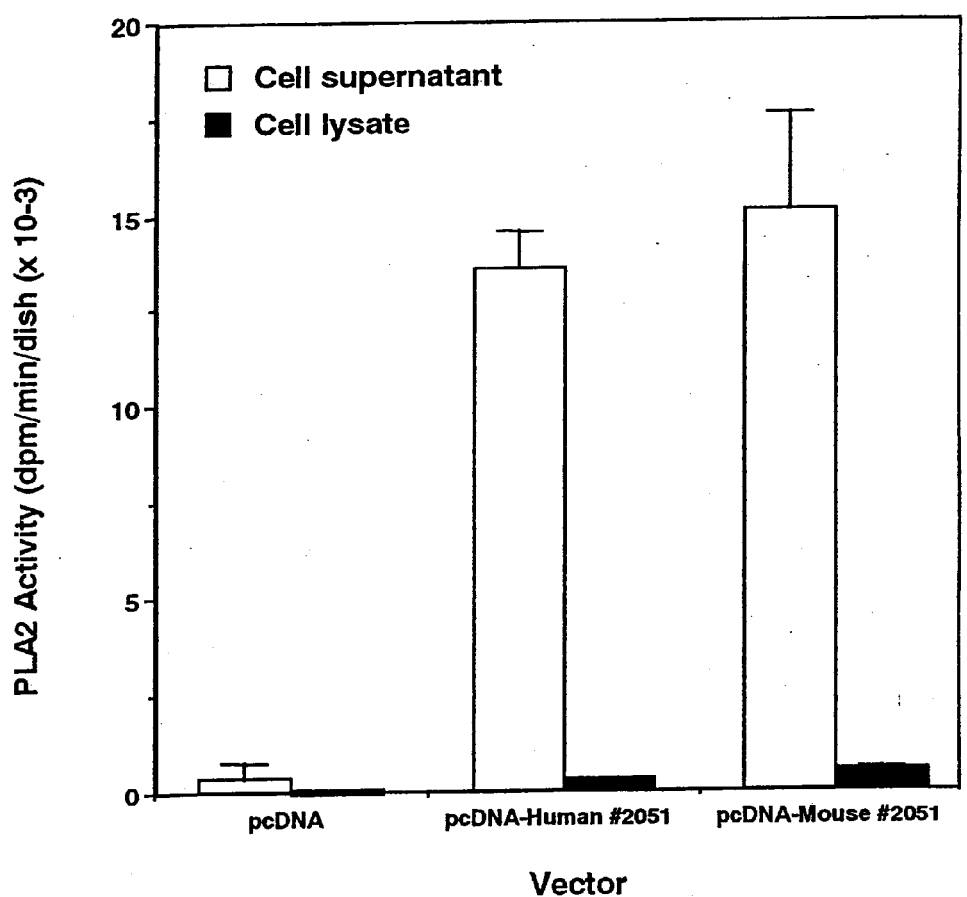
FIG. 2 shows $PLA_2$ activities of the transformants. pcDNA-Mouse IID has the DNA encoding mouse $PLA_2$ (pcDNA-Mouse #2051). pcDNA-Human IID has the DNA encoding human $PLA_2$ (pcDNA-Human #2051). pcDNA does not have $PLA_2$ gene.
Figure 3:
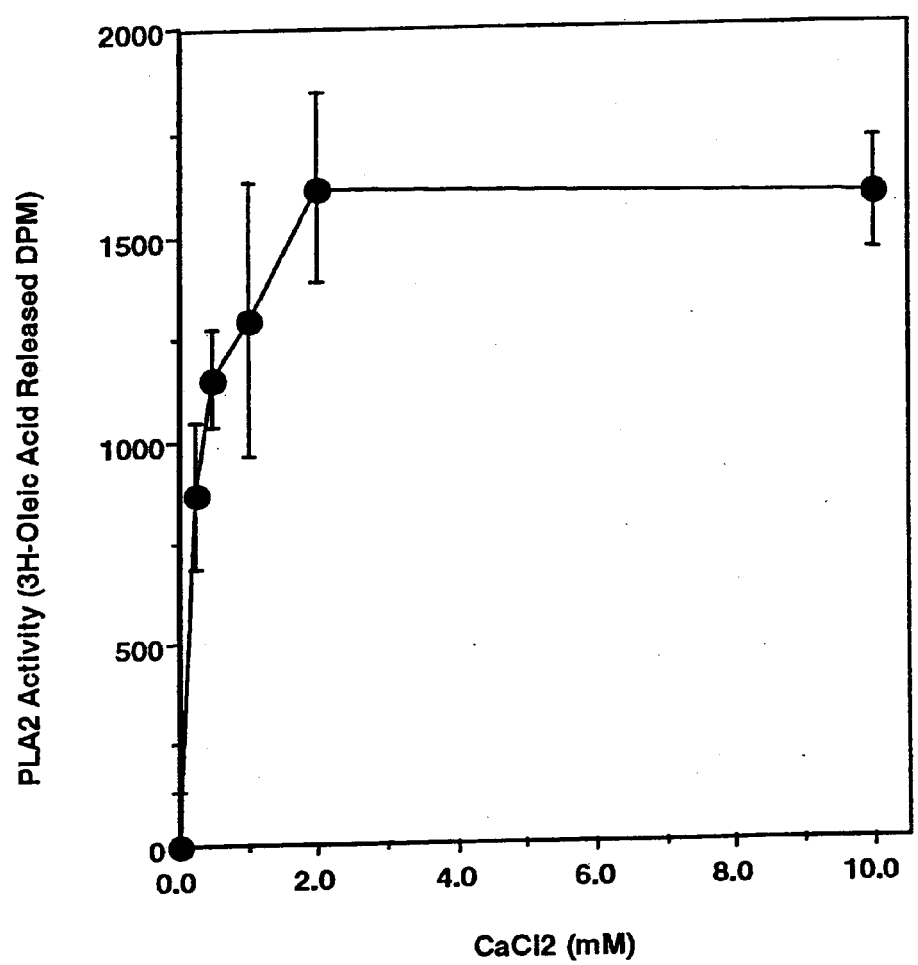
FIG. 3 shows the $Ca^{2+}$ dependence for $PLA_2$ activity in the supernatant of the transformant having the gene encoding the human $PLA_2$ of this invention.

The $PLA_2$ expressing vector was prepared by insertion of this cDNA into pcDNA 3.1(+) (Invitrogen) at the down stream of its promoter in the right direction (the sites between NotI and XbaI sites). The base sequence from the promoter to $PLA_2$ cDNA was determined again to confirm the absence of artificial mutation. Then, the $PLA_2$ expressing vector was inserted into COS-7 cells, the established cell line originated from monkey kidney. Transfection was performed with LipofectAMINE transfection reagent (Gibco BRL) according to the method of the manufacture's instruction. At three days after the transfection, $PLA_2$ activities in the culture supernatant and the cell lysates were measured. Measurement of $PLA_2$ activities was carried out according to the Elsbach et al.'s method (Methods Enzymol. 197, 24–31 (1991)) using 3H-oleate-labeled E. coli membrane phospholipid fractions as the substrate. Significantly high $PLA_2$ activities were detected in the culture supernatant compared with the supernatant in the cultured cells in which a control plasmid with no cDNA of the $PLA_2$ were transfected (FIG. 2). In addition, high concentration of $Ca^{2+}$ was required for the exertion of the enzymatic activities (FIG. 3).

Example 6

Screening for a Compound that Inhibits PLA$_2$ Activity

Inhibitory activity against this novel type of human secretory type PLA$_2$ was determined with Indoxam that is a 1-oxamoylindolidine derivative. It has already been reported that Indoxam inhibits the enzymatic activities of IIA type and IB type secretory type PLA$_2$ (Yokota et al., Biochim. Biophys. Acta (1999) 1438, 213–222). The PLA$_2$ activities were determined by the measurement of the quantity of released $^{14}$C-oleic acid from $^{14}$C-labeled 1-palmitoyl-2-oleoyl-phosphatidylcholine (POPC), according to the Draheim et al.'s method (J. Med. Chem., (1996) 39, 5159–5175). In the solution composed of 50 mM Tris-HCl (pH 8.0), 200 mM NaCl, 2 mM CaCl$_2$, and 1 mg/ml bovine serum albumin, the substrates composed of 1 mM POPC (the mixture of about 100,000 cpm $^{14}$C-POPC and unlabeled POPC) and 3 mM deoxycholic acid were incubated with each secretory PLA2 in the presence of various concentrations of Indoxam at 40° C. for 60 min. Then, the quantity of released $^{14}$C-oleic acid was measured. Purified materials were used in the case with human IB type (2 ng), IIA type (10 ng) and X type (4 ng). Human V type and the secretory type PLA$_2$ of this invention (IID type) were prepared from the culture supernatant of CHO cells that stably express them.

Figure 4:
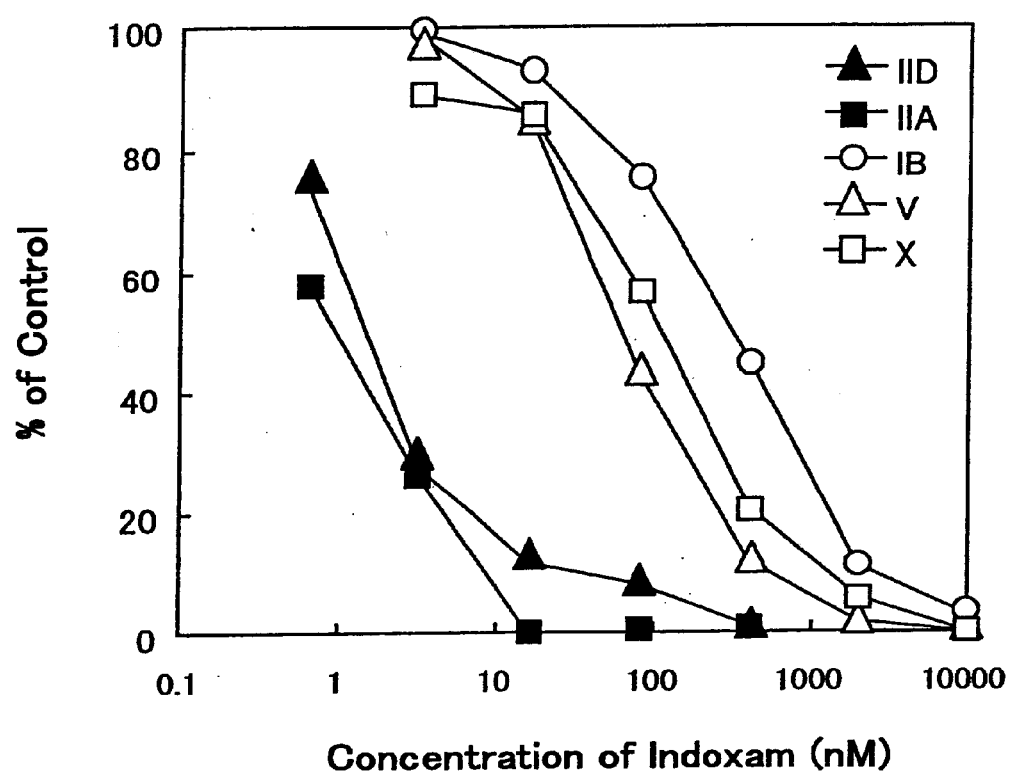
FIG. 4 shows the inhibiting activities for secretory type PLA2 includes the human $PLA_2$ (IID) of this invention by Indoxam.

The quantity of released $^{14}$C-oleic acid from $^{14}$C-POPC by each human secretory type PLA$_2$ in the absence of Indoxam was regarded as 100% and the quantity of released $^{14}$C-oleic acid in the presence of each concentration of Indoxam was shown as %. As the result, it was conformed that Indoxam strongly inhibits the enzymatic activities of both human PLA$_2$ of this invention (IID type ) and IIA type (FIG. 4)

INDUSTRIAL APPLICABILITY

This invention provides human secretory type PLA$_2$; a DNA encoding human secretory type PLA$_2$; a vector including the DNA; a transformant having the vector; a method for producing human secretory type PLA$_2$ using the transformant.

An analytic mean for this secretory type PLA$_2$-related diseases and a screening mean for a specific inhibitory compound against this enzyme are provided by using the secretory type PLA$_2$ of this invention. An assay using an antibody for the enzyme can be applied to the diagnosis of various diseases.

---

What is claimed is:

1. An isolated polypeptide that has phospholipase A2 activity that is encoded by a nucleic acid sequence that hybridizes to the complement of SEQ ID NO: 26 under stringent conditions, wherein stringent conditions comprise heating at 42° C. in 6×SSC, 0.5% SDS and 50% formamide and washing at 68° C. in 0.1×SSC and 0.5% SDS.

2. An isolated polypeptide that has phospholipase A2 activity that comprises SEQ ID NO: 27.

3. The polypeptide of claim 2 consisting of SEQ ID NO: 27.

4. The polypeptide of claim 1 that is a fragment of SEQ ID NO: 27.

5. The polypeptide of claim 1 that comprises amino acid residues 1 to 125 of SEQ ID NO: 27.

6. The polypeptide of claim 1 that comprises residues −20 to 125 of SEQ ID NO: 27.

7. The polypeptide of claim 1 that is a recombinant polypeptide expressed in a prokaryotic cell.

8. The polypeptide of claim 1 that is a recombinant polypeptide expressed in a eukaryotic cell.

9. A composition comprising the polypeptide of claim 1.

10. A composition comprising the polypeptide of claim 1 and a substrate, wherein said polypeptide is immobilized on said substrate.

11. The composition of claim 10, wherein said substrate is an insoluble polysaccharide.

12. The composition of claim 10, wherein said substrate is a synthetic resin.

13. The composition of claim 10, wherein said substrate is glass.

14. The composition of claim 10, wherein said substrate is silicon.

15. A diagnostic reagent comprising the polypeptide of claim 1.

16. An assay kit comprising the polypeptide of claim 1.

* * * * *

SEQUENCE LISTING

<160> NUMBER OF SEQ ID NOS: 29

<210> SEQ ID NO 1
<211> LENGTH: 501
<212> TYPE: DNA
<213> ORGANISM: Mus musculus
<220> FEATURE:
<221> NAME/KEY: misc_feature
<222> LOCATION: (5)..(5)
<223> OTHER INFORMATION: n = c, g, a, or t

<400> SEQUENCE: 1

```
gcggntataa ctgcaaccca gggagggctc ctgaacctga acaagatggt cacacacatg      60
acggggaaga aagccttctt cagctactgg ccctacggct gtcactgtgg acttggtggc     120
aaagggcaac ccaaagatgc cacagactgg tgctgtcaga agcatgattg ttgctatgcc     180
cacctgaaga tcgatggatg caagagcctg acagacaact acaaatacag catctcccag     240
ggcactatcc agtgctctga caacgggagc tggtgtgaaa ggcaactgtg tgcttgtgac     300
aaggaggtgg ccttgtgctt gaagcaaaac ctggatagct acaataagcg cctgcgttac     360
tactggcggc cccgttgcaa aggcaagact ccagcatgct aagggagtcc actctgtctg     420 tccctggat tccaccctgt cctgggacat ctcaagcatt gaagtcctgc agcttgctgc     480
tcccactctg gtgtctagtc t                                               501
```

<210> SEQ ID NO 2
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 2

```
ctcctgaacc tgaacaagat ggtcacac                                         28
```

```
<210> SEQ ID NO 3
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
agagtgggag cagcaagctg caggac                                    26

<210> SEQ ID NO 4
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
cctgaacctg aacaagatgg tcacacac                                  28

<210> SEQ ID NO 5
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
tccaggggac agacagagtg gactcc                                    26

<210> SEQ ID NO 6
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gtgggcatag caacaatcat gcttc                                     25

<210> SEQ ID NO 7
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
ttgccaccaa gtccacagtg acag                                      24

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
cccacacagc agggcgagtc tcat                                      24

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: SYNTHETIC DNA
```

-continued

```
<400> SEQUENCE: 9
ggcactatcc agtgctctga caac                                              24

<210> SEQ ID NO 10
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
aaaggcaact gtgtgcttgt gacaa                                             25

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 11 ataagggggct gcctgccttg ct                                               22

<210> SEQ ID NO 12
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
gaaagttgtt tattaagagg gctctt                                            26

<210> SEQ ID NO 13
<211> LENGTH: 1233
<212> TYPE: DNA
<213> ORGANISM: Mus musculus
<220> FEATURE:
<221> NAME/KEY: CDS
<222> LOCATION: (36)..(467)
<223> OTHER INFORMATION:
<221> NAME/KEY: mat_peptide
<222> LOCATION: (93)..()
<223> OTHER INFORMATION:

<400> SEQUENCE: 13 ataagggggct gcctgccttg ctctgggctg gaact atg aga ctc gcc ctg ctg          53
                                      Met Arg Leu Ala Leu Leu
                                                          -15 tgt ggg ctg ctg ctg gcc ggt ata act gca acc cag gga ggg ctc ctg         101
Cys Gly Leu Leu Leu Ala Gly Ile Thr Ala Thr Gln Gly Gly Leu Leu
        -10              -5               -1  1 aac ctg aac aag atg gtc aca cac atg acg ggg aag aaa gcc ttc ttc         149
Asn Leu Asn Lys Met Val Thr His Met Thr Gly Lys Lys Ala Phe Phe
     5                  10                  15 agc tac tgg ccc tac ggc tgt cac tgt gga ctt ggt ggc aaa ggg caa         197
Ser Tyr Trp Pro Tyr Gly Cys His Cys Gly Leu Gly Gly Lys Gly Gln
 20                  25                  30                  35 ccc aaa gat gcc aca gac tgg tgc tgt cag aag cat gat tgt tgc tat         245
Pro Lys Asp Ala Thr Asp Trp Cys Cys Gln Lys His Asp Cys Cys Tyr
                 40                  45                  50 gcc cac ctg aag atc gat gga tgc aag agc ctg aca gac aac tac aaa         293
Ala His Leu Lys Ile Asp Gly Cys Lys Ser Leu Thr Asp Asn Tyr Lys
             55                  60                  65
```

```
tac agc atc tcc cag ggc act atc cag tgc tct gac aac ggg agc tgg     341
Tyr Ser Ile Ser Gln Gly Thr Ile Gln Cys Ser Asp Asn Gly Ser Trp
            70                  75                  80 tgt gaa agg caa ctg tgt gct tgt gac aag gag gtg gcc ttg tgc ttg     389
Cys Glu Arg Gln Leu Cys Ala Cys Asp Lys Glu Val Ala Leu Cys Leu
 85                  90                  95 aag caa aac ctg gat agc tac aat aag cgc ctg cgt tac tac tgg cgg     437
Lys Gln Asn Leu Asp Ser Tyr Asn Lys Arg Leu Arg Tyr Tyr Trp Arg
100                 105                 110                 115 ccc cgt tgc aaa ggc aag act cca gca tgc taagggagtc cactctgtct       487
Pro Arg Cys Lys Gly Lys Thr Pro Ala Cys
                120                 125 gtccctgga ttccaccctg tcctgggaca tctcaagcat tgaagtcctg cagcttgctg    547
cctcccactc tggtgtctag tctcctggac cagctggctt tcaaggtct ccttgcaaaa    607 gggcctggcc ttgaggactt cctcttggtg cctttctact gtaaaggacc cttttgatct   667
ttctaacggt gacactcctc tcccttcaaa ctctggtctt tctggaccaa ggtcagagct   727
cagccctctg atgctgtgtt ctcccccaac taagctatga gacctctagg ttcagccctg   787
ccccatttca gattccgtgg taccctctgg tggtaccttg attcaggagt ccctagaac    847 caagcccatt atgggctcca acaacaacgg gatttaaggg tgggggaagt tgcagtcttg   907
ttgcactggg tggtcctgg agcttggcct gctgtttctt gcccgttgtg ctttcgctgg    967
gatctcttgc tgcataatag ctcaggctcc ggggccgtcc tttggaagcc tctcttggct  1027
agccattctc cccagcgcta aggacatcat tgggctggac tgtctgggtg gcatcacagc  1087
ccacatttct cctgagacca ggatgataga tgttccagta ctttgtctca tcccaggcct  1147
ggtttctttc tctggaaact ttctccaaag agccctctta ataaacaact ttcacaaaaa  1207
aaaaaaaaaa aaaaaaaaaa aaaaa                                       1233
```

<210> SEQ ID NO 14
<211> LENGTH: 144
<212> TYPE: PRT
<213> ORGANISM: Mus musculus

<400> SEQUENCE: 14

```
Met Arg Leu Ala Leu Leu Cys Gly Leu Leu Ala Gly Ile Thr Ala
            -15                 -10                 -5

Thr Gln Gly Gly Leu Leu Asn Leu Asn Lys Met Val Thr His Met Thr
         -1   1               5                  10

Gly Lys Lys Ala Phe Phe Ser Tyr Trp Pro Tyr Gly Cys His Cys Gly
         15                  20                  25

Leu Gly Gly Lys Gly Gln Pro Lys Asp Ala Thr Asp Trp Cys Cys Gln
 30                  35                  40                  45

Lys His Asp Cys Cys Tyr Ala His Leu Lys Ile Asp Gly Cys Lys Ser
                 50                  55                  60

Leu Thr Asp Asn Tyr Lys Tyr Ser Ile Ser Gln Gly Thr Ile Gln Cys
                 65                  70                  75

Ser Asp Asn Gly Ser Trp Cys Glu Arg Gln Leu Cys Ala Cys Asp Lys
         80                  85                  90

Glu Val Ala Leu Cys Leu Lys Gln Asn Leu Asp Ser Tyr Asn Lys Arg
 95                 100                 105

Leu Arg Tyr Tyr Trp Arg Pro Arg Cys Lys Gly Lys Thr Pro Ala Cys
110                 115                 120                 125
```

<210> SEQ ID NO 15

```
<211> LENGTH: 44
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
agtagttgat gcggccgcca ccatgagact cgccctgctg tgtg            44

<210> SEQ ID NO 16
<211> LENGTH: 38
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
taagcttttc tagattagca tgctggagtc ttgccttt                   38

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
acagactggt gctgtcagaa                                       20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
catgactgtt gctatgccca                                       20

<210> SEQ ID NO 19
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
acacagttgc ctttcacacc a                                     21

<210> SEQ ID NO 20
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
ttcacaccag ctcccgttgt c                                     21

<210> SEQ ID NO 21
<211> LENGTH: 76
<212> TYPE: DNA
<213> ORGANISM: Homo sapiens

<400> SEQUENCE: 21
cctgaagacc caggggtgcg gcatctacaa ggactattac agatacaact tttcccaggg   60
```

```
gaacatccac tgctct                                                      76

<210> SEQ ID NO 22
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 22
agagcagtgg atgttcccct g                                                21

<210> SEQ ID NO 23
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 23
tgtagatgcc gcacccctgg g                                                21

<210> SEQ ID NO 24
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 24
acctgaagac ccaggggtgc g                                                21

<210> SEQ ID NO 25
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 25
cttttcccag gggaacatcc ac                                               22

<210> SEQ ID NO 26
<211> LENGTH: 878
<212> TYPE: DNA
<213> ORGANISM: Homo sapiens
<220> FEATURE:
<221> NAME/KEY: CDS
<222> LOCATION: (29)..(463)
<223> OTHER INFORMATION:
<221> NAME/KEY: mat_peptide
<222> LOCATION: (89)..()
<223> OTHER INFORMATION:

<400> SEQUENCE: 26
tctgcctcca ctgctctgtg ctgggatc atg gaa ctt gca ctg ctg tgt ggg        52
                                Met Glu Leu Ala Leu Leu Cys Gly
                                            -20             -15 ctg gtg gtg atg gct ggt gtg att cca atc cag ggc ggg atc ctg aac      100
Leu Val Val Met Ala Gly Val Ile Pro Ile Gln Gly Gly Ile Leu Asn
        -10                 -5                  -1  1 ctg aac aag atg gtc aag caa gtg act ggg aaa atg ccc atc ctc tcc      148
Leu Asn Lys Met Val Lys Gln Val Thr Gly Lys Met Pro Ile Leu Ser
5                   10                  15                  20 tac tgg ccc tac ggc tgt cac tgc gga cta ggt ggc aga ggc caa ccc      196
```

```
Tyr Trp Pro Tyr Gly Cys His Cys Gly Leu Gly Gly Arg Gly Gln Pro
            25                  30                  35 aaa gat gcc acg gac tgg tgc tgc cag acc cat gac tgc tgc tat gac    244
Lys Asp Ala Thr Asp Trp Cys Cys Gln Thr His Asp Cys Cys Tyr Asp
            40                  45                  50 cac ctg aag acc cag ggg tgc ggc atc tac aag gac tat tac aga tac    292
His Leu Lys Thr Gln Gly Cys Gly Ile Tyr Lys Asp Tyr Tyr Arg Tyr
            55                  60                  65 aac ttt tcc cag ggg aac atc cac tgc tct gac aag gga agc tgg tgt    340
Asn Phe Ser Gln Gly Asn Ile His Cys Ser Asp Lys Gly Ser Trp Cys
 70                  75                  80 gag cag cag ctg tgt gcc tgt gac aag gag gtg gcc ttc tgc ctg aag    388
Glu Gln Gln Leu Cys Ala Cys Asp Lys Glu Val Ala Phe Cys Leu Lys
 85                  90                  95                 100 cgc aac ctg gac acc tac cag aag cga ctg cgt ttc tac tgg cgg ccc    436
Arg Asn Leu Asp Thr Tyr Gln Lys Arg Leu Arg Phe Tyr Trp Arg Pro
                105                 110                 115 cac tgc cgg ggg cag acc cct ggg tgc tagaagccca caccctctac          483
His Cys Arg Gly Gln Thr Pro Gly Cys
                120                 125 cctgttcctc agcatggagc tctggcatcc ccacctcagt atctaacctg aaccagcctg   543
gcttttcaaa cactccgggg ggaggtagtc ccagcctccc ccggaaccct ctaccaatgc   603
cttctgacct tctgaagctt tccgaatcct cccagttgag gcagtagctg tgtcctctga   663
gggtggatgg gaatcttggg agaagccaa gcaagggagc catcagaggt ggtgtttgga    723
ccaaagcatc ggggtgggg agggtctgc cgctgtcccc cgcctgctgg ccccttgtc     783 cttcctcacc ccctccaata tagtctcgga gctgcaaccg cagcagccac tataaagggc   843
aatattaaaa aaaaaaaaaa aaaaaaaaaa aaaaa                              878
```

<210> SEQ ID NO 27
<211> LENGTH: 145
<212> TYPE: PRT
<213> ORGANISM: Homo sapiens

<400> SEQUENCE: 27

```
Met Glu Leu Ala Leu Leu Cys Gly Leu Val Val Met Ala Gly Val Ile
-20              -15                 -10                 -5

Pro Ile Gln Gly Gly Ile Leu Asn Leu Asn Lys Met Val Lys Gln Val
            -1  1               5                   10

Thr Gly Lys Met Pro Ile Leu Ser Tyr Trp Pro Tyr Gly Cys His Cys
            15                  20                  25

Gly Leu Gly Gly Arg Gly Gln Pro Lys Asp Ala Thr Asp Trp Cys Cys
 30                  35                  40

Gln Thr His Asp Cys Cys Tyr Asp His Leu Lys Thr Gln Gly Cys Gly
 45                  50                  55                  60

Ile Tyr Lys Asp Tyr Tyr Arg Tyr Asn Phe Ser Gln Gly Asn Ile His
                 65                  70                  75

Cys Ser Asp Lys Gly Ser Trp Cys Glu Gln Gln Leu Cys Ala Cys Asp
             80                  85                  90

Lys Glu Val Ala Phe Cys Leu Lys Arg Asn Leu Asp Thr Tyr Gln Lys
             95                 100                 105

Arg Leu Arg Phe Tyr Trp Arg Pro His Cys Arg Gly Gln Thr Pro Gly
    110                 115                 120

Cys
125
```

```
<210> SEQ ID NO 28
<211> LENGTH: 44
<212> TYPE: DNA
<213> ORGANISM: ARTIFICIAL SEQUENCE
<220> FEATURE:
<223> OTHER INFORMATION: SYNTHETIC DNA

<400> SEQUENCE: 28
agtagttgat gcggccgcca ccatggaact tgcactgctg tgtg                    44

<210> SEQ ID NO 29
<211> LENGTH: 36
<212> TYPE: DNA
<213> ORGANISM: Homo sapiens

<400> SEQUENCE: 29
taagcttttc tagactagca cccagggggtc tgcccc                            36
```